United States Patent
Roth

(10) Patent No.: US 11,359,458 B2
(45) Date of Patent: Jun. 14, 2022

(54) MONITORING OIL HEALTH IN SUBSURFACE SAFETY VALVES

(71) Applicant: Saudi Arabian Oil Company, Dhahran (SA)

(72) Inventor: Brian A. Roth, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 64 days.

(21) Appl. No.: 16/909,140

(22) Filed: Jun. 23, 2020

(65) Prior Publication Data

US 2021/0396095 A1  Dec. 23, 2021

(51) Int. Cl.
| | |
|---|---|
| *E21B 34/14* | (2006.01) |
| *E21B 34/10* | (2006.01) |
| *E21B 34/16* | (2006.01) |
| *E21B 47/06* | (2012.01) |
| *E21B 47/07* | (2012.01) |

(Continued)

(52) U.S. Cl.
CPC .............. *E21B 34/14* (2013.01); *E21B 34/10* (2013.01); *E21B 34/16* (2013.01); *E21B 47/06* (2013.01); *E21B 47/07* (2020.05); *G01N 1/2035* (2013.01); *G01N 33/2888* (2013.01); *E21B 2200/05* (2020.05); *G01N 2001/205* (2013.01)

(58) Field of Classification Search
CPC .......... E21B 34/14; E21B 34/16; E21B 47/06; E21B 47/07; E21B 34/10; E21B 2200/05; G01N 1/2035; G01N 33/2888; G01N 2001/205
See application file for complete search history.

(56) References Cited

U.S. PATENT DOCUMENTS

| | | | |
|---|---|---|---|
| 4,227,573 A | 10/1980 | Pearce et al. | |
| 4,728,882 A | 3/1988 | Stanbro et al. | |

(Continued)

FOREIGN PATENT DOCUMENTS

| | | |
|---|---|---|
| GB | 958734 | 5/1964 |
| GB | 2302114 | 1/1997 |

(Continued)

OTHER PUBLICATIONS

GCC Examination Report issued in Gulf Cooperation Council Appln. No. 2020-39164, dated Jun. 24, 2021, 5 pages.

(Continued)

*Primary Examiner* — Michael R Wills, III
(74) *Attorney, Agent, or Firm* — Fish & Richardson P.C.

(57) ABSTRACT

A subsurface safety valve for controlling fluid flow in a wellbore including a monitoring sub having a hydraulic connection port and defining a piston bore. The monitoring sub defining a hydraulic circuit extending between the hydraulic connection port and the piston bore. The monitoring sub comprising a sensing assembly incorporated in the hydraulic circuit that is operable to measure a degradation level of fluid in the hydraulic circuit. A flapper sub attached to the monitoring sub. A piston disposed in the piston bore of the monitoring sub. A flow tube positioned between the monitoring sub and the flapper attached to a downhole end of the monitoring sub and in contact with the flapper, the flow tube having a protrusion in contact with the piston. A return spring positioned in a cavity defined between the flow tube and the flapper sub, biasing the flow tube towards the monitoring sub.

19 Claims, 9 Drawing Sheets

(51) Int. Cl.
*G01N 1/20* (2006.01)
*G01N 33/28* (2006.01)

(56) References Cited

U.S. PATENT DOCUMENTS

| | | | |
|---|---|---|---|
| 5,597,042 A | 1/1997 | Tubel et al. | |
| 5,752,569 A | 5/1998 | Bhavsar et al. | |
| 5,754,055 A | 5/1998 | McAdoo et al. | |
| 5,973,503 A | 10/1999 | Kuipers et al. | |
| 6,138,764 A * | 10/2000 | Scarsdale | E21B 23/08 |
| | | | 166/117.6 |
| 6,199,629 B1 | 3/2001 | Shirk et al. | |
| 6,216,784 B1 | 4/2001 | Harrell | |
| 6,392,562 B1 | 5/2002 | Boston et al. | |
| 6,459,995 B1 | 10/2002 | Collister | |
| 6,535,001 B1 | 3/2003 | Wang | |
| 6,590,402 B2 | 7/2003 | Wang et al. | |
| 6,718,819 B2 | 4/2004 | Schoess | |
| 7,129,715 B2 | 10/2006 | Hayashi et al. | |
| 8,508,741 B2 | 8/2013 | Kumar | |
| 8,522,604 B2 | 9/2013 | Zhe et al. | |
| 9,804,076 B2 | 10/2017 | Harrell et al. | |
| 2004/0084189 A1 | 5/2004 | Hosie et al. | |
| 2004/0250606 A1 | 12/2004 | Buttgenbach et al. | |
| 2006/0076149 A1 | 4/2006 | McCalvin | |
| 2006/0105467 A1 | 5/2006 | Niksa et al. | |
| 2009/0120168 A1 | 5/2009 | Harrison et al. | |
| 2009/0153155 A1 | 6/2009 | Chambon et al. | |
| 2010/0109686 A1 | 5/2010 | Zhe et al. | |
| 2010/0263856 A1 | 10/2010 | Lynde et al. | |
| 2012/0073829 A1 * | 3/2012 | Smith | E21B 34/10 |
| | | | 166/375 |
| 2014/0024073 A1 | 1/2014 | Zhdaneev et al. | |
| 2014/0116117 A1 | 5/2014 | Joksch | |
| 2014/0158347 A1 | 6/2014 | Fielder et al. | |
| 2014/0158350 A1 | 6/2014 | Castillo et al. | |
| 2015/0075802 A1 * | 3/2015 | Cowman | E21B 47/07 |
| | | | 166/336 |
| 2015/0209782 A1 | 7/2015 | Mostowfi et al. | |
| 2016/0195509 A1 | 7/2016 | Jamieson et al. | |
| 2016/0363575 A1 | 12/2016 | Von Herzen et al. | |
| 2017/0089166 A1 | 3/2017 | Sullivan | |
| 2018/0051700 A1 | 2/2018 | Sheth et al. | |
| 2018/0347346 A1 | 12/2018 | Gouda et al. | |
| 2019/0204291 A1 | 7/2019 | Potyrailo et al. | |
| 2020/0096431 A1 | 3/2020 | Nie et al. | |
| 2020/0141506 A1 * | 5/2020 | Holder | F16K 17/30 |
| 2021/0010995 A1 | 1/2021 | Roth | |

FOREIGN PATENT DOCUMENTS

| | | |
|---|---|---|
| GB | 2302349 | 1/1997 |
| NO | 20140453 | 10/2015 |
| WO | WO 2009090466 | 7/2009 |
| WO | WO 2009137316 | 11/2009 |
| WO | WO 2014151967 | 9/2014 |
| WO | WO 2020002946 | 1/2020 |

OTHER PUBLICATIONS

PCT Invitation to Pay Additional Fees in International Appln. No. PCT/US2021/038635, dated Sep. 15, 2021, 16 pages.

PCT International Search Report and Written Opinion in International Appln. No. PCT/US2020/041329, dated Oct. 22, 2020, 15 pages.

Aghayan, "On-Line Monitoring of Engine Health through the Analysis of Containments in Engine Lubricant," University of Western Ontario (Graduate Program in Mechanical and Material Engineering), May 2012, 274 pages.

Kauffman, "Rapid, Portable Voltammetric Techniques for Performing Antioxidant, Total Acid Number (TAN) and Total Base Number (TBN) Measurements," Technology Showcase: Integrated Monitoring, Diagnostics and Failure Prevention, Proceedings of a Joint Conference, Apr. 22-26, 1996, 13 pages.

Meredith et al., "Influence of biodegradation on crude oil acidity and carboxylic acid composition," Organic Geochemistry vol. 31, 2000, 15 pages.

Wang, "Engine oil condition sensor: method for establishing correlation with total acid number," Sensors and Actuators B, vol. 86, 2002, 5 pages.

Wilson, "Determination of the asphaltene and carboxylic acide content of a heavy oil using a microfluidic device," Lab on a Chip, Apr. 2009, 6 pages.

Zhang, "A novel on-chip impedance sensor for the detection of particle contamination in hydraulic oil," micromachines, MDPI, Aug. 14, 2017, 15 pages.

GCC Examination Report issued in Gulf Cooperation Council Appln. No. 2020-40064, dated Oct. 12, 2021, 4 pages.

PCT International Search Report and Written Opinion in International Appln. No. PCT/US2021/038635, dated Nov. 8, 2021, 20 pages.

* cited by examiner

MONITORING OIL HEALTH IN SUBSURFACE SAFETY VALVES

TECHNICAL FIELD

The present disclosure generally relates to monitoring fluids of wellbore equipment, more particularly monitoring oil health in subsurface safety valves.

BACKGROUND

Oil and gas subsurface well tools may be installed either temporarily, semi-permanently, or permanently. Logging tools are considered temporary with time-in-hole measured in hours or days. Semi-permanent equipment includes electrical submersible pumps with limited life in the well, measured in months or years. Permanent equipment includes downhole gauges, inflow control valves, subsurface safety valves, and wellhead equipment including subsea trees. This equipment is permanently installed with completion tubing. It can contain protective fluid in the tool cavity that can provide lubrication for bearings, heat dissipation for electrical equipment, or dielectric protection for electrical and electronic equipment.

With time, heat, and possible contamination from the production environment, the tool cavity protective fluid in the equipment degrades. When the fluid has degraded past its useful life, it can lead to failure of the tool. In subsurface safety valves, a volume of hydraulic fluid is transferred in and out of the subsurface safety valve with applied surface pressure actuating and moving the downhole piston open and closed. The transferring of fluid in and out of the subsurface safety valves creates a potential for fluid degradation.

SUMMARY

This specification describes implementation of microfluidic lab-on-a-chip devices in subsurface safety valves assembly to monitor oil quality. Specifically, microfluidic lab-on-a-chip devices allow the evaluation of hydraulic fluid in the downhole safety valve assembly. The hydraulic fluid is passed through the microfluidic device using the hydraulic pressure from the surface and circulates through a fluid channel in the microfluidic device. The fluid quality is evaluated by various sensing methods.

A method to evaluate the oil health of a downhole safety valve is disclosed. The method includes flowing, by a sensor or a fluid moving device secured to a safety valve assembly disposed at a downhole location within a wellbore, a portion of hydraulic fluid of the safety valve through a body of the sensor. The portion of the hydraulic fluid is exposed to the body of the sensor responsive to the fluid flow. Since the hydraulic fluid cannot be removed once the hydraulic line is installed, excessive fluid degradation can take place. Fluid degradation occurs due to the presence of contamination within the control line and it can be caused by communication with the wellbore. The degraded fluid remains in the system through the downhole piston and can prevent proper operation of the subsurface safety valve. The method can also include, in response to the hydraulic fluid being exposed to the body of the sensor, determining, at least in part by the sensor, a degradation level of the hydraulic fluid. The method can also include transmitting, by the sensor or a device communicatively coupled to the sensor, the determined degradation level to a surface of the wellbore.

A subsurface safety valve is a critical device in the well. The subsurface safety valve prevents the flow of hydrocarbons to the surface during an unanticipated or uncontrolled well event. The subsurface safety valve typically is attached to a dedicated pressurized hydraulic fluid line from the surface to actuate a downhole piston against a spring. The spring is located between the downhole piston and a flapper within the subsurface safety valve assembly. The subsurface safety valve remains open by a hydraulic pressure sent from a control panel at the surface. In the event of an emergency shutdown, the hydraulic pressure is released and the subsurface safety valve is closed. This prevents the release of hydrocarbons and other fluids and gases to the surface.

During operation, opening and closing of the piston is a dynamic hydraulic event. The dynamic seals on the piston isolate the clean hydraulic fluid from the contaminated production fluid. Opening and closing of the piston allow a portion of the contaminated fluid to mix with the clean hydraulic fluid. Over time, the clean hydraulic fluid becomes contaminated and impairs the proper operation of the piston and prevents the subsurface safety valve from fail-safe closing.

The cleanliness level of the hydraulic fluid is also affected by a sudden closure of the subsurface safety valve. Typical hydraulic fluid includes a cleanliness level of SAE AS4059 Class 6 or above. A sudden closure imposes an impact on the tubing string in the form of a water hammer and releases debris present in the hydraulic control line. The contaminated fluid impairs the proper operation of the piston and prevents the subsurface safety valve from fail-safe closing.

The disclosed implementation of a microfluidic analyzer in the subsurface safety valve allows early detection of fluid contamination that results in the extended operational life of the valve, or replacement of the valve before failure from the fluid degradation.

The microfluidic analyzer evaluates fluid degradation using particle count method. Hydraulic fluid would be passed through the microfluidic analyzer on each applied pressure cycle. The microfluidic circuit is bypassed during the release of hydraulic pressure to enable rapid closing of the subsurface safety valve. Data obtained from the microfluidic analyzer is captured and transmitted to the surface with a dedicated communication line. Analysis of the data is performed in real-time at the surface with an alarm or trigger when the results pass a specific threshold.

An example implementation of the subject matter described within this disclosure is a subsurface safety valve for controlling fluid flow in a wellbore with the following features. A monitoring sub having a hydraulic connection port and defining a piston bore, the monitoring sub defining a hydraulic circuit extending between the hydraulic connection port and the piston bore, the monitoring sub comprising a sensing assembly incorporated in the hydraulic circuit that is operable to measure a degradation level of fluid in the hydraulic circuit. A flapper sub attached to the monitoring sub, the flapper sub having a body and a flapper, the flapper pivotable between an open position allowing flow through subsurface safety valve and a closed position limiting flow through the subsurface safety valve. A piston disposed in the piston bore of the monitoring sub. A flow tube positioned between the monitoring sub and the flapper of the attached to a downhole end of the monitoring sub and in contact with the flapper, the flow tube having a protrusion in contact with the piston. A return spring positioned in a cavity defined between the flow tube and the flapper sub, the return spring in contact with the flow tube and biasing the flow tube towards the monitoring sub.

Aspects of the example implementation, which can be combined with the example implementation alone or in combination, include the following. The hydraulic circuit comprises: a first channel that extends from hydraulic connection port to the piston bore with a check valve installed in the first channel that prevents flow from the hydraulic connection port to the piston bore through the first channel. A second channel that branches off the first channel at a first junction between the hydraulic port and the check valve and rejoins the first channel at second junction between the check valve and the piston bore.

Aspects of the example implementation, which can be combined with the example implementation alone or in combination, include the following. The sensing assembly is disposed in the second channel.

Aspects of the example implementation, which can be combined with the example implementation alone or in combination, include the following. Compensation bellows disposed in the second channel between the first junction and the sensing assembly.

Aspects of the example implementation, which can be combined with the example implementation alone or in combination, include the following. A filter disposed between the second junction and the check valve.

Aspects of the example implementation, which can be combined with the example implementation alone or in combination, include the following. The sensing assembly comprises a plurality of components operable to measure the degradation level of the fluid in the fluid circuit.

Aspects of the example implementation, which can be combined with the example implementation alone or in combination, include the following. The plurality of components comprises an optical source and a photometer.

Aspects of the example implementation, which can be combined with the example implementation alone or in combination, include the following. The plurality of components comprises a conductor and a magnet.

Aspects of the example implementation, which can be combined with the example implementation alone or in combination, include the following. The plurality of components comprises an impedance sensor that includes an internal micro-channel and two single-layer coils.

Aspects of the example implementation, which can be combined with the example implementation alone or in combination, include the following. The plurality of components comprises a microfluidic circuit and a sensor, wherein the microfluidic circuit includes microchannel and two capacitance plates.

Aspects of the example implementation, which can be combined with the example implementation alone or in combination, include the following. The sensing assembly is configured to transmit a determined degradation level by transmitting at least one of a voltage output, a current output, a pressure output, a time stamp, or a temperature output measured by the sensing assembly.

An example implementation of the subject matter described within this disclosure is a subsurface safety valve for controlling fluid flow in a wellbore with the following features. A monitoring sub defining a hydraulic circuit extending through the monitoring sub, the monitoring sub comprising a sensing assembly incorporated in a hydraulic circuit that is operable to measure a degradation level of fluid in the hydraulic circuit. A safety valve configured to be disposed downhole of the monitoring sub and in hydraulic communication with the monitoring sub. A closure mechanism moveable between an open position allowing flow through subsurface safety valve and a closed position limiting flow through the subsurface safety valve. A piston in contact with the closure mechanism and operable to move the closure mechanism between its open and closed positions, the piston hydraulically activated by pressure applied to the piston by pressure transmitted through hydraulic circuit of the monitoring sub.

Aspects of the example implementation, which can be combined with the example implementation alone or in combination, include the following. The monitoring sub is attached to the safety valve and the hydraulic circuit extends between a hydraulic connection port of the monitoring sub and a piston bore defined by the monitoring hub.

Aspects of the example implementation, which can be combined with the example implementation alone or in combination, include the following. The hydraulic circuit comprises: a first channel that extends from hydraulic connection port to the piston bore with a check valve installed in the first channel that prevents flow from the hydraulic connection port to the piston bore through the first channel. A second channel that branches off the first channel at a first junction between the hydraulic port and the check valve and rejoins the first channel at second junction between the check valve and the piston bore.

Aspects of the example implementation, which can be combined with the example implementation alone or in combination, include the following. The sensing assembly is disposed in the second channel.

Aspects of the example implementation, which can be combined with the example implementation alone or in combination, include the following. Compensation bellows disposed in the second channel between the first junction and the sensing assembly.

Aspects of the example implementation, which can be combined with the example implementation alone or in combination, include the following. The sensing assembly comprises a plurality of components operable to measure the degradation level of the fluid in the fluid circuit.

Aspects of the example implementation, which can be combined with the example implementation alone or in combination, include the following. The sensing assembly is configured to transmit a determined degradation level by transmitting at least one of a voltage output, a current output, a pressure output, a time stamp, or a temperature output measured by the sensing assembly.

Aspects of the example implementation, which can be combined with the example implementation alone or in combination, include the following. The plurality of components comprises an optical source and a photometer.

Aspects of the example implementation, which can be combined with the example implementation alone or in combination, include the following. The closure mechanism comprises a flapper pivotable between an open position allowing flow through subsurface safety valve and a closed position limiting flow through the subsurface safety valve.

A method to evaluate the oil health of a subsurface safety valve is disclosed. A microfluidic analyzer chip also called "lab-on-a-chip" similar to the one from RAB-Microfluidics may be installed in the hydraulic fluid cavity within the body of the safety valve, or a separate chamber. The fluid is passed through the microfluidic analyzer chip with the application of hydraulic pressure from the surface and circulates through the fluid channel in the microfluidic analyzer. Fluid quality is evaluated by electrical (resistance or capacitance), electromagnetic, mechanical, electrical admittance, optic, pressure with fiber-optic Bragg grating, or other methods used with microfluidic analyzers.

The details of one or more embodiments of these systems and methods are set forth in the accompanying drawings and the description below. Other features, objects, and advantages of these systems and methods will be apparent from the description and drawings, and from the claims.

DETAILED DESCRIPTION

This specification describes implementation of downhole systems (e.g., microfluidic lab-on-a-chip devices) in subsurface safety valves assembly to monitor oil quality. For example, microfluidic lab-on-a-chip devices can allow evaluation of a hydraulic fluid in the downhole safety valve assembly. The hydraulic fluid is passed through the microfluidic device, using the hydraulic pressure from the surface, and circulates through the fluid channel in the microfluidic device. The fluid quality is evaluated by various sensing methods.

A method to evaluate the oil health of a downhole safety valve is disclosed. The method includes flowing, by a sensor or a fluid moving device secured to a safety valve assembly disposed at a downhole location within a wellbore, a portion of a hydraulic fluid of the safety valve through a body of the sensor. The portion of the hydraulic fluid is exposed to the body of the sensor responsive to the fluid flow. Since the hydraulic fluid cannot be removed once the hydraulic line is installed, excessive fluid degradation can take place. Fluid degradation occurs due to presence of contamination within the control line and it is caused by communication with the wellbore. The degraded fluid remains in the system through the downhole piston and prevents the subsurface safety valve from proper operation. The method also includes, in response to the hydraulic fluid being exposed to the body of the sensor, determining, at least in part by the sensor, a degradation level of the hydraulic fluid. The method also includes transmitting, by the sensor or a device communicatively coupled to the sensor, the determined degradation level to a surface of the wellbore.

Figure 1:
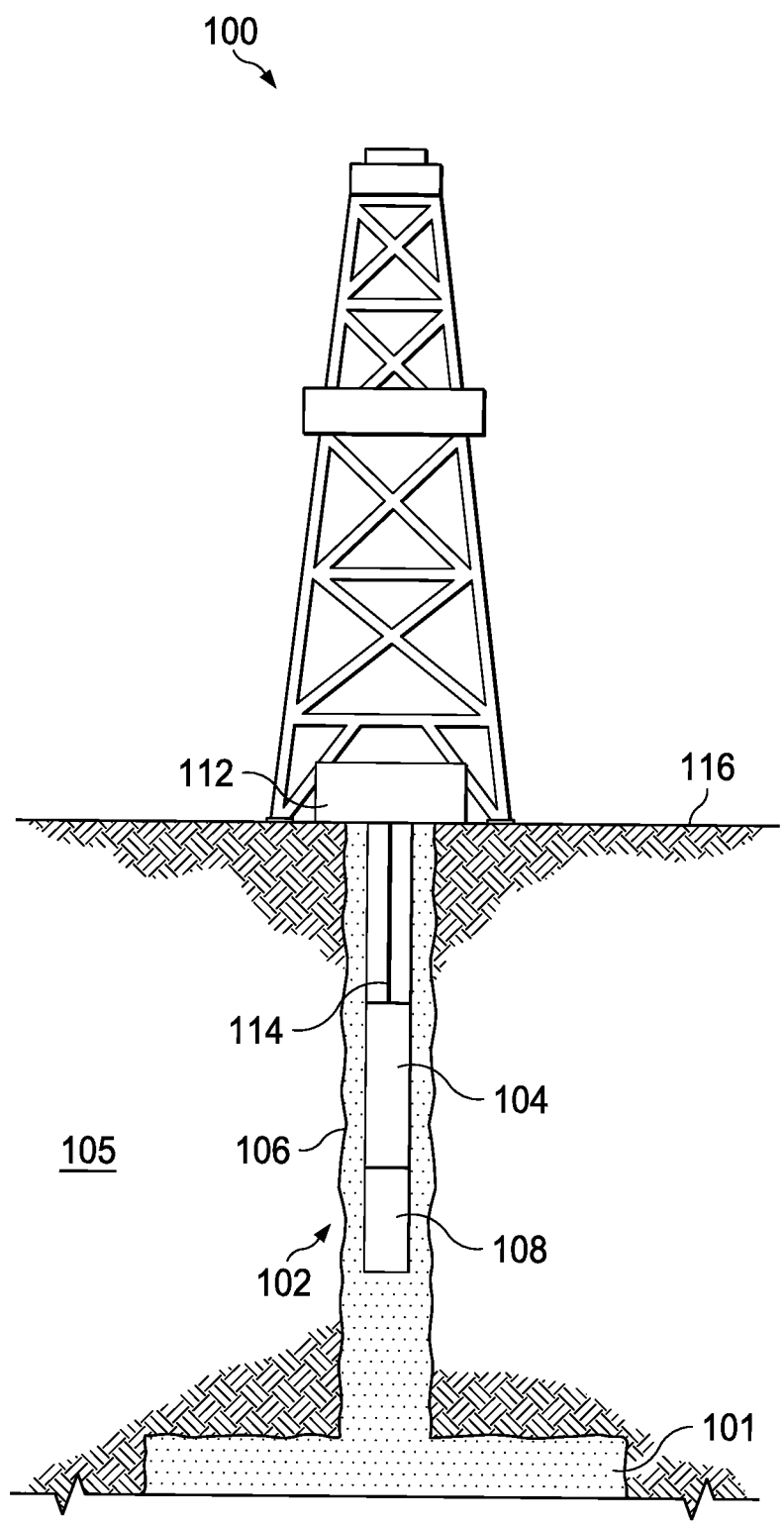
FIG. 1 is a cross-sectional, schematic view of a monitoring system deployed in a wellbore.

FIG. 1 is a cross-sectional, schematic view of a monitoring system 100 deployed in a wellbore 106. A method and a system 100 for monitoring a protective fluid of a pump (for example, an ESP) 104 is shown. The monitoring system 100 includes an ESP assembly 102 disposed at a downhole location within a wellbore 106 formed in a geologic formation 105. The geologic formation 105 includes a hydrocarbon reservoir 101 from which hydrocarbons can be extracted. The ESP assembly 102 features a pump 104 and a monitoring sub 108. The system 100 also includes a communication line 114 and a receiver 112. The communication line 114 connects the monitoring sub 108 to the receiver 112. The receiver 112 can be on the wellhead or at a different location at the surface 116 of the wellbore 106. The receiver 112 can include a processor configured to process the information received from the monitoring sub 108.

Wellbore tools such as logging tools can be considered temporary, with lifetime in the wellbore 106 measured in hours or days. Permanent equipment or tools may include downhole gauges, inflow control valves, subsurface safety valves, and wellhead equipment including subsea trees. Semi-permanent wellbore tools include equipment such as ESPs, which have a limited lifetime in the well, with expected duration measured in months or years. Some of these wellbore tools may contain protective fluid in cavities of the tool to provide lubrication for bearings, heat dissipation for electrical equipment, or dielectric protection for electrical and electronic equipment. With time, heat and possible contamination from the production environment can cause the protective fluid in the equipment to degrade. Without knowing the degradation level of the protective fluid, the fluid can degrade past its useful life and can lead to failure of an associated wellbore tool.

Figure 3:
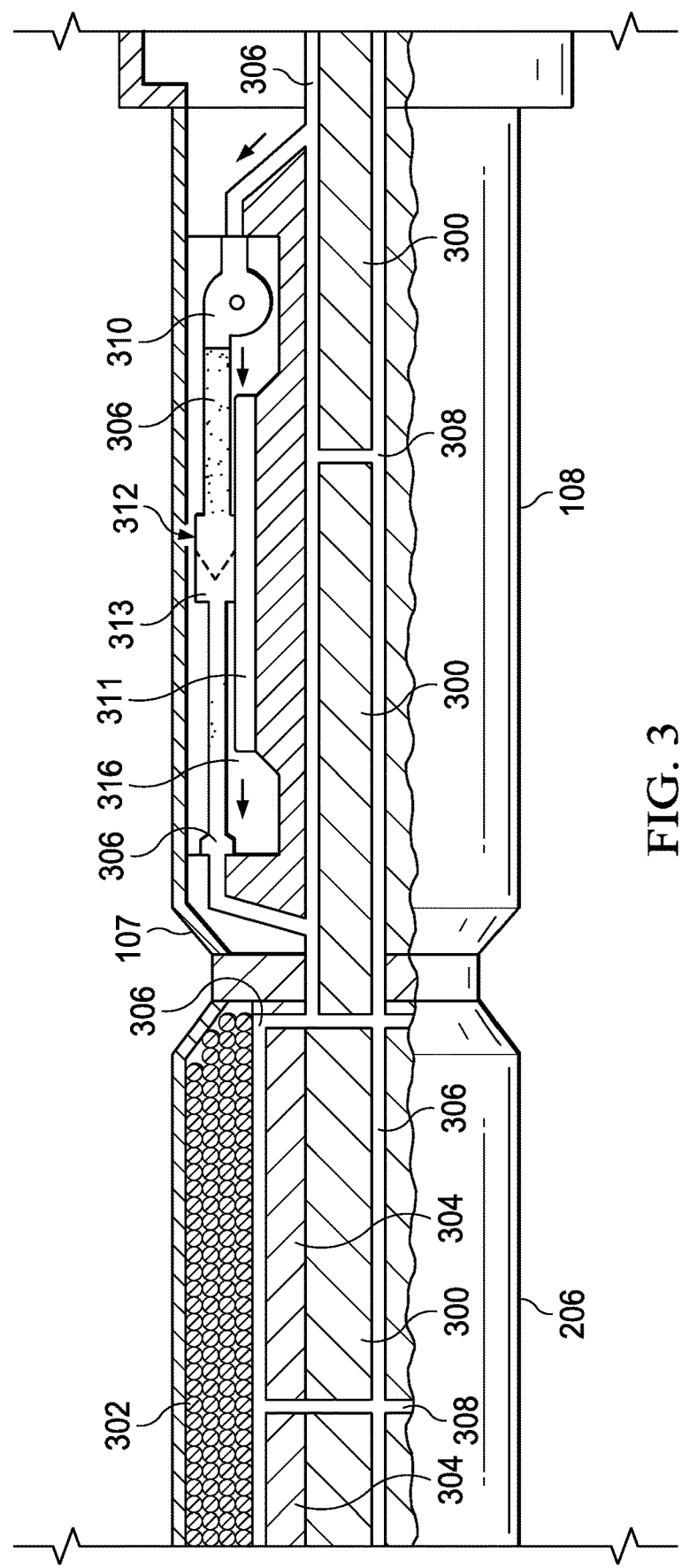
FIG. 3 shows a partial cross-sectional view of an ESP and a monitoring sub.

In the production environment (for example, inside the wellbore, the wellhead, or the reservoir) of oil and gas, some equipment or wellbore tools may be deployed temporarily, semi-permanently, or permanently. The technology described in this disclosure can be implemented in wellbore tools regardless of their respective lifetime. As shown in FIG. 3, a sensor 312 exposed to a protective fluid 306 can determine the degradation level or the quality of the fluid 306. For example, the sensor 312 can be or include a 'lab-on-a-chip' that includes a microfluidic device (for example, a microfluidic analyzer) coupled to a surface of a wellbore tool. The lab-on-a-chip can be used to analyze the protective fluid 306 of the tool and determine a degradation level of the protective fluid 306. The lab-on-a-chip supports decisions regarding replacing the protective fluid of the downhole tools or similar maintenance-related decisions to prevent the failure of the wellbore tool. The degradation level determined by the sensor can be transmitted, in some implementations, to the monitoring sub 108. As shown in FIG. 1, the monitoring sub 108 is communicatively connected to the wellbore surface 116 (for example, a receiver at the surface) via communication line 114 (or wirelessly). The monitoring sub 108 can transmit the degradation level determined by the microfluidic device to the surface 116. For example, the monitoring sub 108 can transmit, along with other ESP or SSSV data, the degradation level to receiver 112. In some implementations, the data received can be analyzed in real time at the surface, and alarms or triggers can be activated if the degradation level is above a specific threshold. By "real time," it is meant that a duration between receiving an input and processing the input to provide an output can be minimal, for example, in the order of milliseconds, microseconds or nanoseconds.

Figure 2:
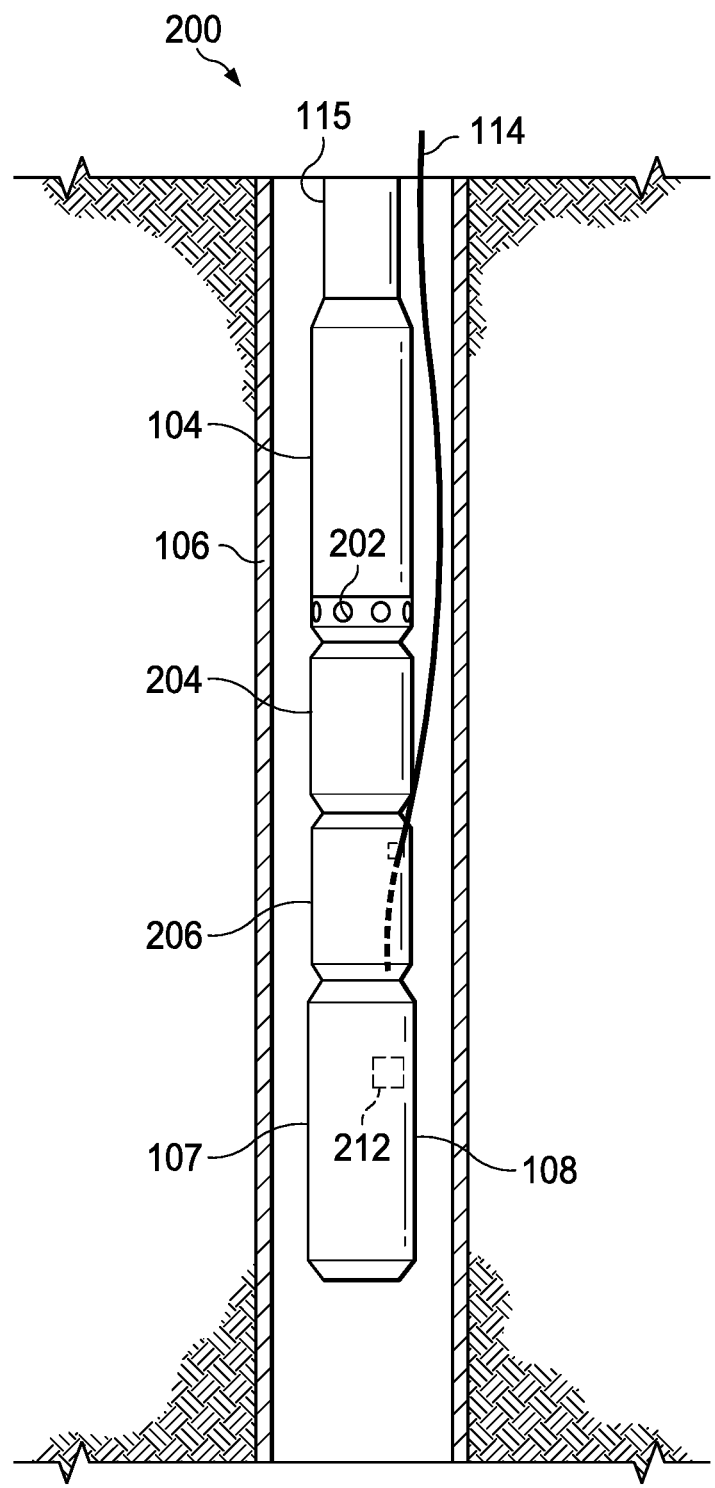
FIG. 2 shows an electric submersible pump (ESP) assembly.

FIG. 2 shows an electric submersible pump (ESP) assembly 200 according to an implementation of the present disclosure. The ESP assembly 200 includes a pump 104, a pump intake 202, a protector 204, a motor 206, and a monitoring sub 108 communicatively connected, via communication line 114 (which may include a power line connected to motor 206), to the surface. The communication line 114 can be coupled to a tubing assembly 115 that connects the ESP assembly to the surface. The monitoring sub 108 is coupled to the motor 206 and can both share the same internal protective fluid. In some implementations, the same protective fluid can be shared among the motor 206, the protector 204, and the monitoring sub 108. The monitoring sub 108 has a housing 107 that protects electronics, cables, sensors, and other components inside the monitoring sub 108. A sensor 212 (for example, a microfluidic device) can be attached to an inner surface of the monitoring sub 108 under the housing 107, adjacent to or separate from the other electronics of the monitoring sub. The housing 107 can form a seal that protects the internal electronics of the monitoring sub from the high pressures at the wellbore. The monitoring sub 108 can transmit to the surface of the wellbore, through line 114, the status of the ESP assembly and other data. In some implementations, the monitoring sub can communicate wirelessly to the surface of the wellbore. Each of the components of the ESP assembly can have common or separate protective fluids that flow internally to protect moving parts and electronics of the components. The conditions at the wellbore cause the protective fluids to degrade. For example, water or other fluids can enter the ESP assembly 200 and contaminate the fluid; wear of rotating components such as bearings or shafts can create particle contamination; or fluid temperature in excess of allowable range or outgassing of downhole electronic components may degrade the protective fluid.

FIG. 3 shows a partial cross-sectional view of an ESP 200 and a monitoring sub 108 according to implementations of the present disclosure. In this embodiment, an internal shaft 300 of the ESP assembly extends through the ESP motor 206 and the monitoring sub 108. In the interest of simplicity, bearings, seals, valves, and other internal components of the ESP assembly are not shown. The ESP motor 206 includes a rotor 304 and a stator 302. The shaft 300, rotor 304, bearings, and other components can be lubricated by the protective fluid 306 that flows around the shaft 300 and the rotor 304. The protective fluid 306 can flow through lubricating holes 308 or grooves of the shaft or of a surface around the shaft to allow the fluid 306 to flow from one side of the shaft to another, and to the rotor 304. The protective fluid 306 can be a dielectric fluid (for example, a liquid dielectric insulator) or a hydraulic fluid (for example, a lubricating hydraulic oil). Multiple protective fluids can flow inside the ESP assembly. The protective fluid 306 also flows around the portion of the shaft 300 if disposed within the monitoring sub 108. The protective fluid 306 can be exposed to a sensor 312 attached to an inner surface of the monitoring sub 108 or to any component of the ESP assembly. As discussed later, the protective fluid 306 can be moved by a fluid moving device 310 or by other techniques to reach the sensor 312.

The sensor 312 includes a microfluidic analyzer that includes a microfluidic device. In some implementations, the microfluidic analyzer can include micro-electro-mechanical systems (MEMS) to perform operations such as pumping fluid, mixing two fluids, heating fluids or other operations. Alternatively or in addition, the microfluidic analyzer can include passive devices, for example, valves, or vias, that can be coupled to actuators, for example, pumps or mixers, to perform operations including analyzing the degradation level of the fluids. For example, the microfluidic analyzer or components of the microfluidic analyzer can be obtained from RAB-Microfluidics Ltd., located in Aberdeen, UK. The microfluidic analyzer includes one or more channels to receive the fluid. The channel is formed on a substrate made of glass, silicon wafer or polydimethylsiloxane (PDMS), for example. MEMS-based actuators are built into the substrate near each channel or actuators are separately connected to the substrate and fluidically coupled to the channel (or both). The sensor 312 can be configured to operate in a horizontal position. For example, in an ESP that operates in a horizontal wellbore, sensor 312 can be horizontally installed in the downhole tool (for example, along the longitudinal axis of the ESP), as shown in FIG. 3. For installation in a vertical well, the sensor 312 can be installed perpendicular to the longitudinal axis of the ESP. Additionally, the sensor 312 can be mechanical isolated by an insulator (for example, a gel or a foam) from the downhole tool to improve the reliability of the measurements.

To monitor a level of degradation of the protective fluid 306, a portion of the sensor 312 is exposed to the protective fluid 306. One or more of these sensors 312 can be rigidly attached to any tool cavity 316 accessible by the protective fluid 306. For example, the sensor 312 can be attached to an inner surface of the ESP 104 along a fluid path of the protective fluid 306. As shown in FIG. 3, the sensor 312 is mounted to and communicatively coupled with the monitoring sub 108 to transmit information to the monitoring sub 108. For example, the sensor 312 can have an electronic board 311 communicatively connected to the monitoring sub 108. The sensor 312 has a body 313 that is exposed and responsive to the protective fluid 306 (for example, a portion of the protective fluid) flowed through the body of the sensor to analyze the protective fluid and determine the level of degradation. The portion of the protective fluid 306 is exposed to the body 313 of the sensor 312 responsive to the sensor 312 or a fluid moving device 310 moving the fluid through the body 313 of the sensor 312. The sensor 312 can be disposed along the natural path of the protective fluid 306 or external to the path of the protective fluid 306, in which cases the fluid moving device 310 can direct the protective fluid 306 toward the sensor. In some implementations, the sensor 312 can be submerged, by a mechanism of the monitoring sub, in the protective fluid 306 to expose the sensor to the fluid. The body 313 of the sensor 312 can sense the protective fluid 306 as the fluid moves across a surface of the body. The sensor 312 can analyze and determine, at least in part, the degradation level of the protective fluid 306 and transmit the degradation level to the monitoring sub 108. For example, responsive to sensing the fluid, the sensor 312 can transmit at least one of a voltage output, a pressure output, and a temperature output to the monitoring sub 108. The monitoring sub 108 can transmit the degradation level to a surface of the wellbore to be analyzed or processed, if necessary.

To expose the sensor 312 to the protective fluid 306, a fluid moving device 310 can flow a portion of the fluid across a body 313 of the sensor 312. The body 313 of the sensor is configured to be responsive to the fluid. In some implementations, the fluid moving device 310 is a small displacement pump such as a peristaltic pump. In some implementations, the fluid moving device 310 is a micropump that moves the fluid with a natural, positive intake pressure, or a vacuum pump that moves the fluid with a negative pressure force on the discharge end of the sensor 312. In some examples, the fluid moving device 310 is an Archimedes screw-type pump. The protective fluid 306 can be actively or passively circulated through the surface of the sensor 312. The fluid moving device 310 can be powered by a power source of the ESP assembly (not shown) or can have its own power source (for example, a battery). In some implementations, the protective fluid 306 can be moved through a sensory convection current or oil convection current. For example, the protective fluid 306 can move due to thermal heating and cooling of the protective fluid 306 that sets up a fluid convection current. The fluid convection current can enable a circulation of the fluid 306 over the sensor.

The sensor 312 can determine the level of degradation of the protective fluid 306 using various methods, and transmit the results with different outputs. For example, the output of the determination performed by the sensor 312 can be a voltage, a pressure, or a temperature. For example, an optical source (such as a laser or light emitting diode) of determined wavelength can be mounted to the monitoring sub 108. The optical source can irradiate the fluid sample in the sensor with light of the determined wavelength so that the dielectric fluid exhibits fluorescence. An intensity of the fluorescence will vary based on contaminants in the fluid. A photometer mounted to the monitoring sub 108 and coupled to the optical source and the sensor will capture that intensity and convert it into a voltage signal. Thus, the output of the sensor can be a magnitude of the voltage signal, which is directly proportional to the intensity of the fluorescence. In some implementations, the sensor 312 (for example, the microfluidic device) performs a portion of the determination and sent that information to the surface, where a receiver (see FIG. 1) performs another portion of the determination. In some implementations, much of the analysis is trend analysis over time. For example, fluid degradation can be measured as a change in an output voltage and compared to a laboratory generated degradation curve of the same fluid.

The sensor 312 can determine the degradation level using at least one of an inductance detection technique and a capacitance change technique. For example, sensor 312 includes a microfluidic analyzer with conductors, magnets, or other components that allow the microfluidic analyzer to sense a change of inductance or capacitance as a portion of the fluid 306 is flowed through the microfluidic analyzer.

Figure 4A:
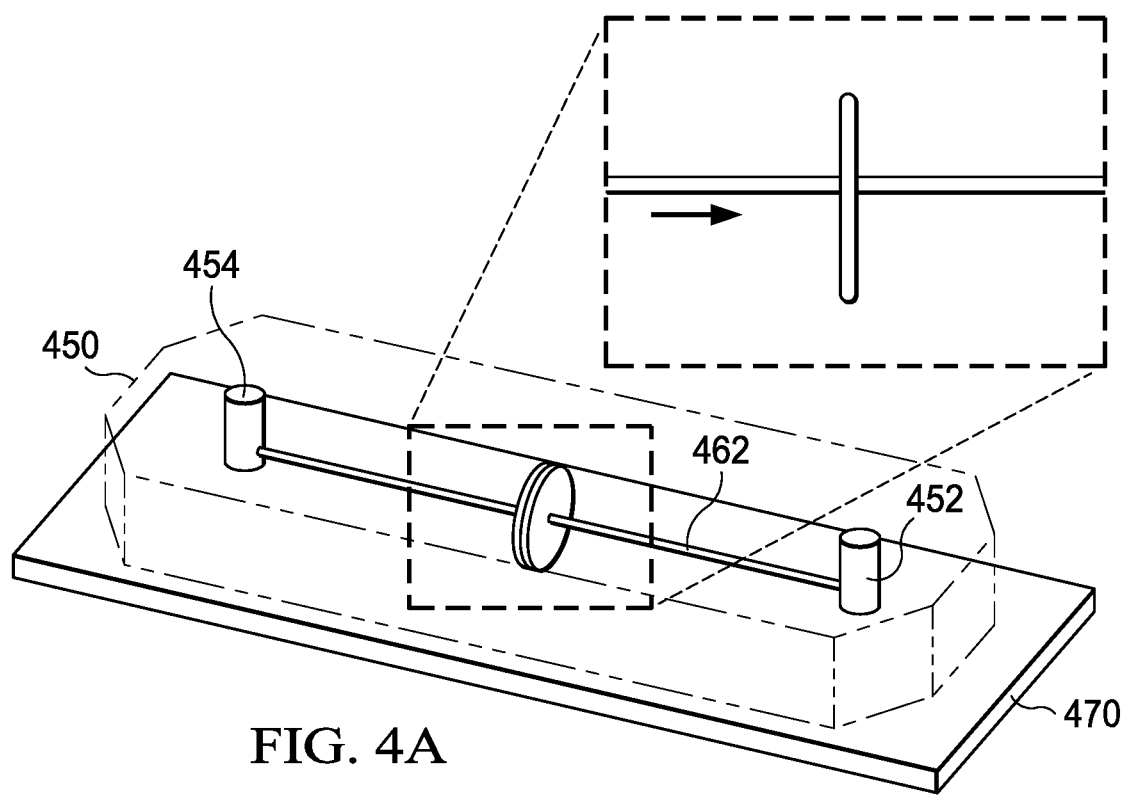
FIGS. 4A-4C show a microfluidic device used in an inductance detection method.
Figure 4B:
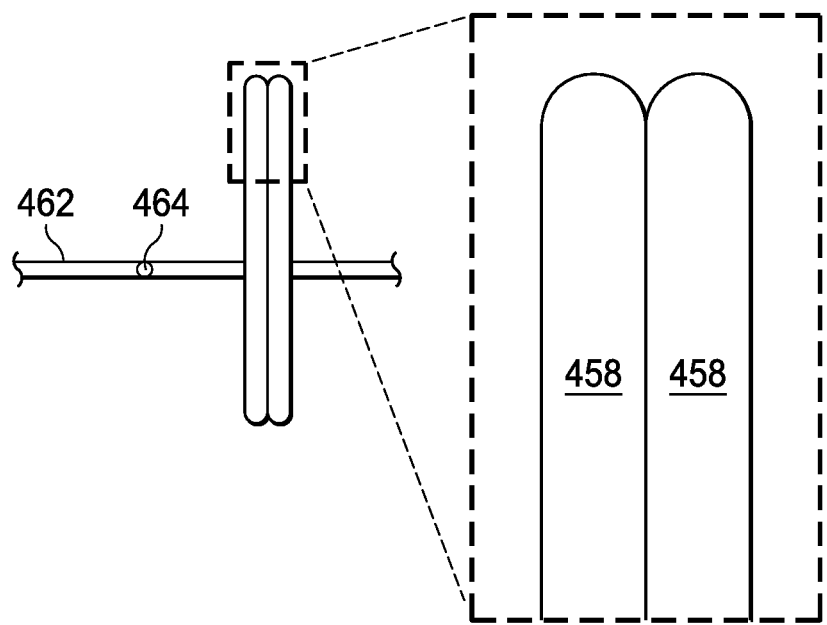
Figure 4C:
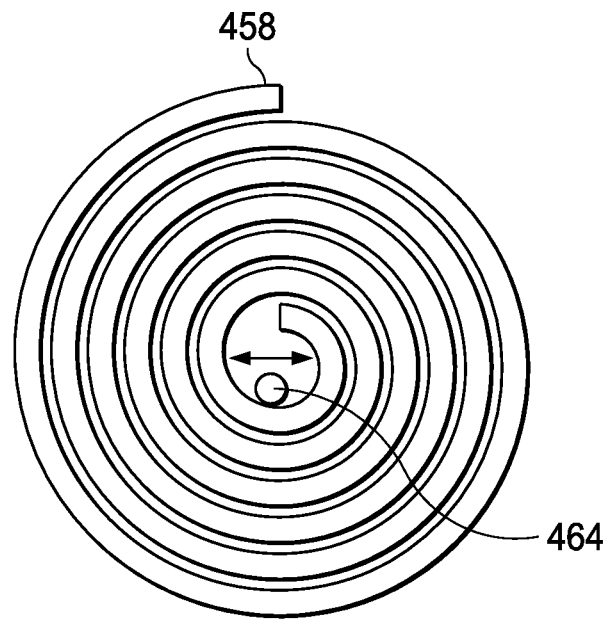

FIGS. 4A-4C show a microfluidic device 470 used in an inductance detection method. For example, a microfluidic chip 470 can be used to determine the particle contamination level. The microfluidic chip 470 can include an impedance sensor 450 having an internal micro-channel 462 surrounded by two single-layer coils 458. Particles 464 of the protective fluid can be moved by the pump (see FIG. 3) from an inlet 454 of the microfluidic chip to an outlet 452 of the microfluidic chip. The particles 464 can be passed through the micro-channel 462 to be sensed by the coils 458 to provide a change in inductance and a measurable increase in the signal to noise ratio. The results can be analyzed by the microfluidic device or external circuitry to provide a particle count to the surface of the wellbore. Sampling can be done continuously or intermittently. The micro-channel can have a diameter of about 300 micrometers (µm), and the coil wire can have an outer diameter of about 900 µm.

Figure 5:
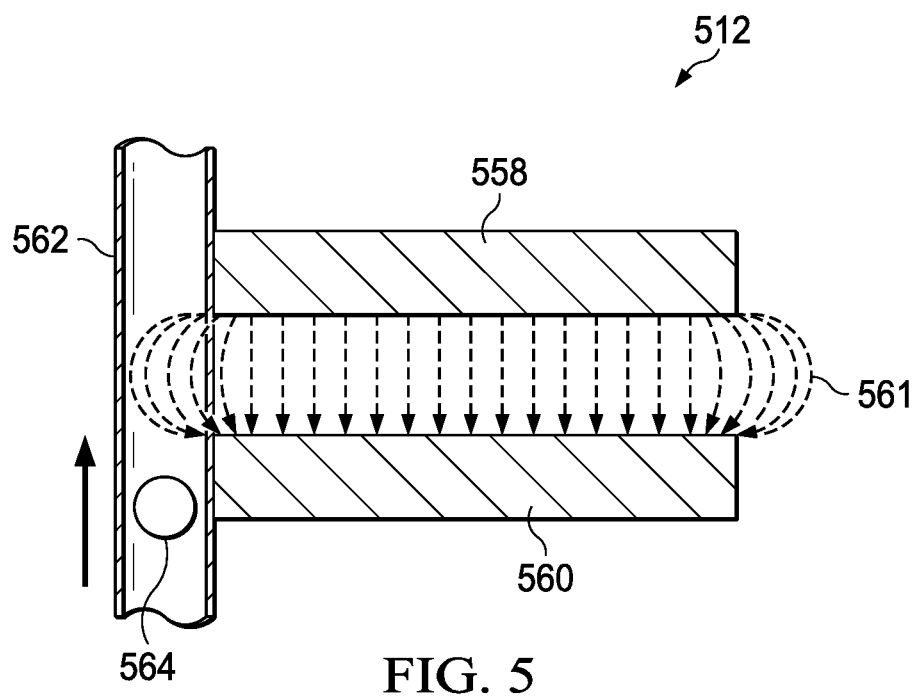
FIG. 5 is a side view of a portion of a microfluidic device used in a capacitance change method.

FIG. 5 is a side view of a portion of a microfluidic device 470 used in a capacitance change method. FIG. 5 shows a similar method to the one described with respect to FIGS. 4A-4C for detecting fluid contamination. Water particles contaminating the protective fluid can be detected using capacitance change. A microfluidic circuit 512 has a micro-channel 562 for particles 564 to move along the channel similar to the inductive circuit and sensor described above with respect to FIGS. 4A-4C. The microfluidic circuit 512 has two capacitance plates 558 and 560 parallel to one another to form an electric field 561 between the plates. As a particle 564 (for example, a water particle) moves adjacent to the plates, a capacitance between the plates changes. The change in capacitance can be analyzed by the microfluidic device or external circuitry to provide the change to the surface of the wellbore. Sampling can be done continuously or intermittently. The capacitor can produce capacitance when the two plates are powered by an alternating current. The principle of capacitance detection is that when a particle passes through the capacitor, the permittivity of media between the plates will change varying the capacitance.

Figure 6:
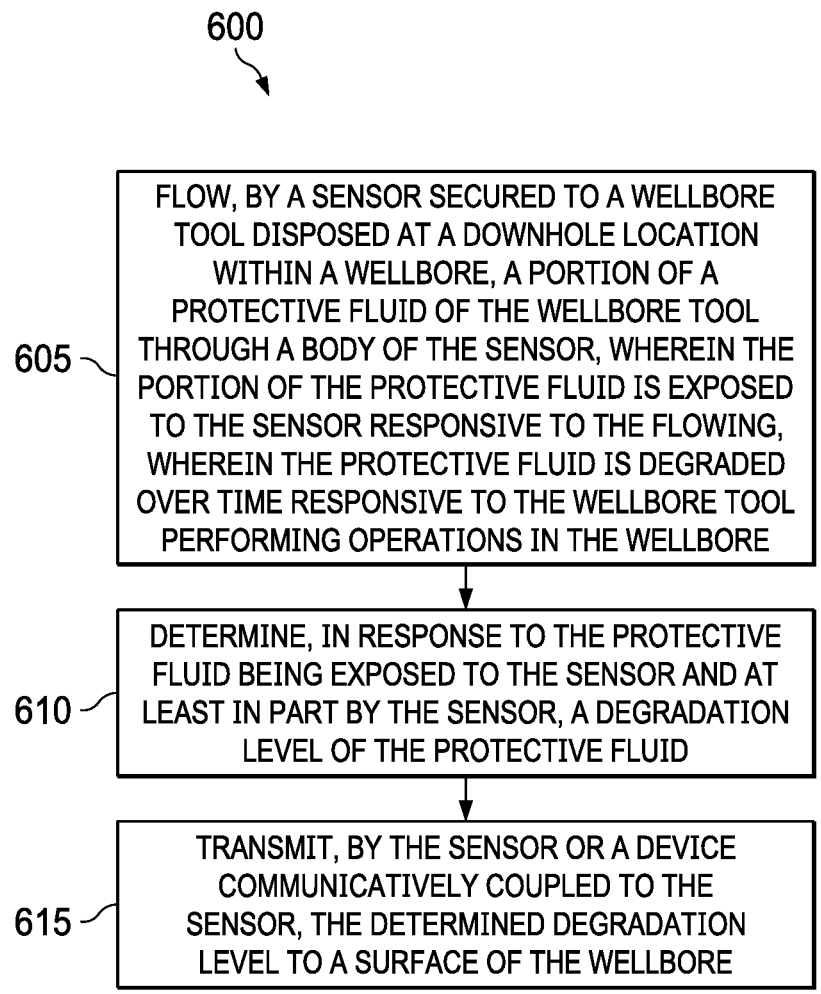
FIG. 6 is a flowchart showing a method of monitoring a protective fluid of a wellbore tool.

FIG. 6 shows a flowchart of a method 600 of monitoring a protective fluid of a wellbore tool. The method includes flowing, by a sensor secured to a wellbore tool disposed at a downhole location within a wellbore, a portion of a protective fluid of the wellbore tool through a body of the sensor, where the portion of the protective fluid is exposed to the sensor responsive to the flowing, where the protective fluid degrades over time responsive to the wellbore tool performing operations in the wellbore (605). The method also includes, in response to the protective fluid being exposed to the sensor, determining, at least in part by the sensor, a degradation level of the protective fluid (610). The method also includes transmitting, by the sensor or a device communicatively coupled to the sensor, the determined degradation level to a surface of the wellbore (615).

Figure 7:
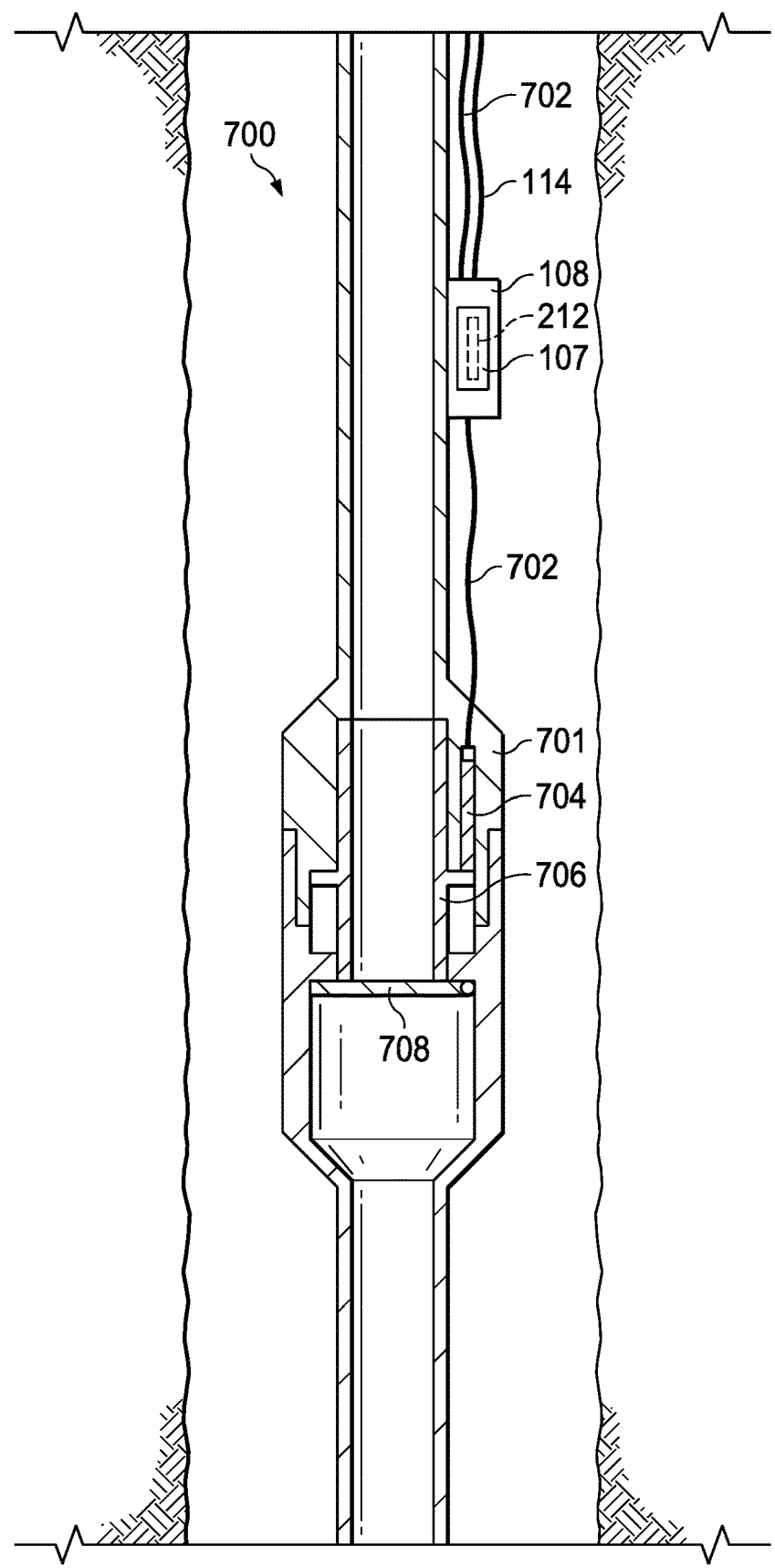
FIG. 7 shows a subsurface safety valve assembly and a monitoring sub deployed at the wellbore.

FIG. 7 shows a subsurface safety valve assembly 700 deployed in a wellbore 106. The subsurface safety valve assembly 700 includes a subsurface safety valve 701 and a monitoring sub 108 in a module separate from the subsurface safety valve 701. Implementations in which the microfluidic analyzer 212 is in a module separate from the subsurface safety valve assembly 700 can be used, for example, with tubing retrievable safety valves. There are two methods to install safety valves in the wellbore. A tubing retrievable valve is installed with the tubing string typically with a Workover Rig. The tubing retrievable valve will incorporate all safety valve embodiments which may or may not include an integral microfluidic analyzer. Another method to install the safety valve is by wireline. A wireline safety incorporates two parts, a ported landing nipple installed with the Workover Rig while the completion is run. The second part is the wireline safety valve which can be installed separate from the rig with wireline. The wireline safety valve will require the microfluidic analyzer to be installed with the Workover Rig.

A hydraulic control line 702 connects the subsurface safety valve assembly 700 to the surface. The subsurface safety valve 701 includes a hydraulic piston 704, a flow tube 706, and a flapper 708. The monitoring sub 108 communicatively connected, via communication line 114 (which may include a power line), to the surface. The communication line 114 can be coupled to a tubing assembly 115 that extends to the surface. The monitoring sub 108 has a housing 107 that protects electronics, cables, sensors, and other components inside the monitoring sub 108. A sensor 212 (for example, a microfluidic device) can be attached to an inner surface of the monitoring sub 108 under the housing 107, adjacent to or separate from the other electronics of the monitoring sub 108. The housing 107 can form a seal that protects the internal electronics of the monitoring sub 108 from the high pressures at the wellbore 106. The monitoring sub 108 can transmit to the surface of the wellbore 106, through line 114, the status of the subsurface safety valve 701 and other data. In some implementations, the monitoring sub 108 communicates wirelessly to the surface of the wellbore 106.

In some implementations, the microfluidic analyzer 212 is in a ported nipple which is a receptacle for a wireline deployed safety valve. A tubing retrievable safety valve can be deployed and retrieved with the well tubing string. Used generally, the term "safety valve" can indicate a tubing retrievable safety valve, the ported nipple and the wireline line deployed safety valve, or other safety valves. Each of the components of the subsurface safety valve assembly 700 can have common or separate protective fluids that flow internally to protect moving parts and electronics of the components. The conditions in the wellbore cause the protective fluids to degrade.

Figure 8:
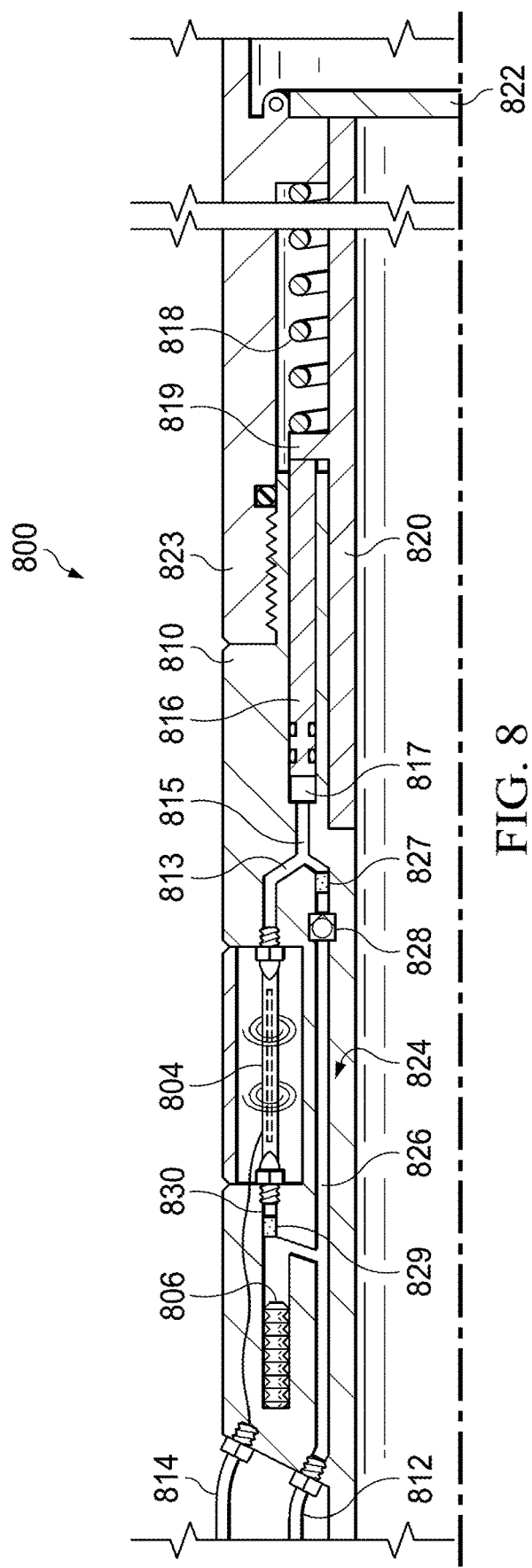
FIG. 8 shows a partial cross-sectional view of a subsurface safety valve assembly and a monitoring sub.

FIG. 8 shows a partial cross-sectional view of a subsurface safety valve 800 with an integral monitoring sub 810 that includes a hydraulic connection port 817. In use, the subsurface safety valve 800 is attached to a hydraulic control line 812 and an electrical communication line 814. The subsurface safety valve 800 includes the monitoring sub 810, a hydraulic actuating piston 816, a resilient member (e.g., a return spring 818), a flow tube 820, and closure mechanism. In the subsurface safety valve 800, the closure mechanism is a flapper 822 hingeably attached to a flapper sub 823. Some safety valves use other closure mechanisms such as ball, or sliding sleeve rather than a flapper.

The hydraulic actuating piston 816 is positioned in a piston bore defined in the monitoring sub 810. The monitoring sub 810 also defines a recess in its inner wall to receive the flow tube 820. An inner wall of the flow tube 820 is aligned with a portion of an inner wall of the monitoring sub 810 that is uphole of the recess. The terms "uphole" and "downhole" are used to indicate the position of components relative to the orientation of the safety valve 800 during use and do not imply a requirement that the system be in a wellbore. The downhole end of the subsurface safety valve 800 is the location of the flapper and the uphole end of the subsurface safety valve 800 is the location of the hydraulic control line 812.

The flow tube 820 extends from a first end received in the recess defined in the inner wall of the monitoring sub 810 to a second end that engages the flapper 822. The flow tube 820 has a protrusion 819 that extends radially outward. The return spring 818 is placed around the flow tube 820 downhole of the protrusion 819. The flapper sub 823 is positioned around the flow tube 820 such that the flapper sub 823 and the flow tube 820 define a cavity holding the return spring 818. The hydraulic actuating piston 816, the return spring 818, the flow tube 820, and the flapper sub 823 are held in place relative to the monitoring sub 810 by threaded engagement between the monitoring sub 810 and the flapper sub 823. The return spring 818 biases the flow tube 820 towards the uphole end of the subsurface safety valve 800 that allows the flapper 822 to close. The flapper 822 is opened by application of hydraulic pressure at the surface to the hydraulic actuating piston 816 to move the flow tube 820 downhole by compressing the return spring 818.

The monitoring sub 810 is pressure containing to withstand external wellbore pressure and fluids. The monitoring sub 810 includes bulkhead connections that provide attachment ports for the hydraulic line 812 and for the electrical communication line 814 which are positioned in an annulus between the well tubing and the well casing.

The monitoring sub 810 defines a branched hydraulic circuit 824 providing a hydraulic connection between the attachment port for the hydraulic line 812 and the bore receiving the hydraulic actuating piston 816. A first channel (e.g., a relief channel 826) provides one-way fluid flow from the cavity receiving the hydraulic actuating piston 816 to the surface 116 without flow restriction. The relief channel 826 contains a high flow check valve 828 to limit (e.g., prevent) flow from the surface 116 to the hydraulic actuating piston 816 through the relief channel 826. The subsurface safety valve 800 includes a filter 827 installed in the relief channel 826 downhole of the check valve to prevent debris or contamination from reaching the check valve 802. This filter is optional and some systems are implemented without it.

A second channel (e.g., testing channel 830) of the hydraulic circuit 824 provides hydraulic communication (i.e., flow and pressure) from the surface 116 to the hydraulic actuating piston 816. The testing channel 830 branches off the relief channel 826 at a first junction 813 between the hydraulic attachment port 817 and the check valve 828 and rejoins the relief channel 826 at a second junction 815 between the check valve 828 and the piston bore.

The testing channel 830 includes a microchannel for the microfluidic analyzer. A separate larger channel in parallel to the microchannel is optional and increases flow rate to the hydraulic actuating piston 816. Fluid flow is initiated by application of pressure at the surface through a surface pump. In the subsurface safety valve 800, the testing channel 830 includes a filter 829 to prevent line blockage by particles larger than the microchannel for the microfluidic analyzer. This filter is optional. The safety valve is a normally closed valve. In order to keep the safety valve open, a hydraulic surface pressure must be constantly applied to the hydraulic actuating piston 816.

Compensation bellows 806 are positioned between the bulkhead connections and the monitoring sub 108. Compensation bellows 806 control the operating mechanism within the subsurface safety valve 800. Compensation bellows 806 allow for hermetical sealing and prevent leakage to the atmosphere. The microchannel channel 830 has limited fluid throughput. The compensating bellows 806 absorbs and slowly dispenses the hydraulic pressure applied at the surface to actuate the piston 816 through the microchannel enabling the sensing assembly to detect fluid contamination.

A sensing assembly of the monitoring sub 810 is substantially similar to the sensing assembly of the monitoring sub 108 discussed with respect to FIGS. 3-5. The monitoring sub 810 includes a microchannel for fluid analysis, a sensor 212, and an electronic board 804 for detection. The electronic board 804 may also be capable of performing data analysis including a required action such as triggering an alarm to perform maintenance. An electrical communication line 814 is able to transmit and receive signals between the electronic board 804 downhole and an alarm or readout at the surface receiver 112. In some implementation, the monitoring sub 108 may be embedded into the body of the subsurface safety valve.

Sensors used for monitoring the health of the fluid include optical, inductance, or capacitance. The sensors can determine the level of fluid degradation using various methods. The sensors transmit the measured results through different outputs such as a voltage, a pressure, or a temperature. Details of the sensor ability to determine fluid degradation and transmit results in a form of various outputs are discussed earlier with reference to FIGS. 3-5.

Figure 9:
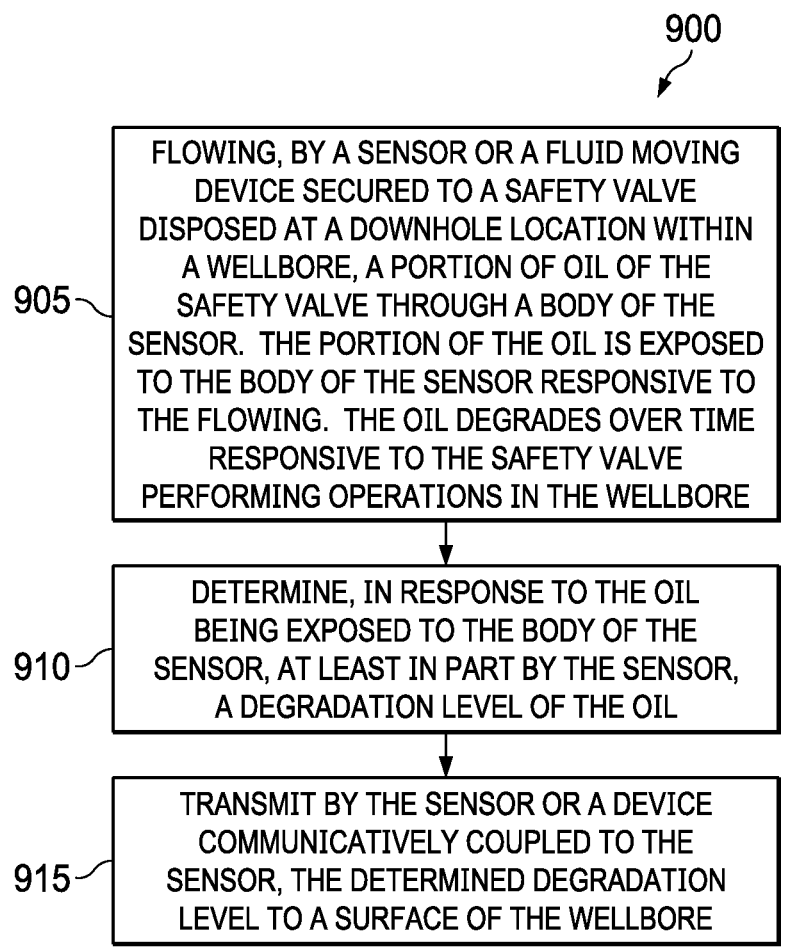
FIG. 9 is a flowchart showing a method of monitoring oil health of a subsurface safety valve assembly.

FIG. 9 shows a flowchart of a method 900 of monitoring fluid health in subsurface safety valve assembly 700. The method 900 includes flowing, by a sensor secured to a safety valve disposed at a downhole location within a wellbore, a portion of fluid within the safety valve through a body of the sensor, where the portion of the fluid is exposed to the sensor responsive to the flowing, where the fluid degrades over time responsive to the safety valve performing operations in the wellbore (905). The method also includes, in response to the fluid being exposed to the sensor, determining, at least in part by the sensor, a degradation level of the fluid (910). The method also includes transmitting, by the sensor or a device communicatively coupled to the sensor, the determined degradation level to a surface of the wellbore (915).

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure. Accordingly, other embodiments are within the scope of the following claims.

What is claimed is:

1. A subsurface safety valve for controlling fluid flow in a wellbore, the subsurface safety valve comprising:
    a monitoring sub having a hydraulic connection port and defining a piston bore, the monitoring sub defining a hydraulic circuit extending between the hydraulic connection port and the piston bore, the hydraulic circuit comprises:
        a first channel that extends from the hydraulic connection port to the piston bore with a check valve installed in the first channel that prevents flow from the hydraulic connection port to the piston bore through the first channel; and
        a second channel that branches off the first channel at a first junction between the hydraulic port and the check valve and rejoins the first channel at second junction between the check valve and the piston bore;
    wherein the monitoring sub comprising a sensing assembly incorporated in the hydraulic circuit that is operable to measure a degradation level of fluid in the hydraulic circuit;
    a flapper sub attached the monitoring sub, the flapper sub having a body and a flapper, the flapper pivotable between an open position allowing flow through subsurface safety valve and a closed position limiting flow through the subsurface safety valve;
    a piston disposed in the piston bore of the monitoring sub;
    a flow tube positioned between the monitoring sub and the flapper of the attached to a downhole end of the monitoring sub and in contact with the flapper, the flow tube having a protrusion in contact with the piston; and
    a return spring positioned in a cavity defined between the flow tube and the flapper sub, the return spring in contact with the flow tube and biasing the flow tube towards the monitoring sub.

2. The subsurface safety valve of claim 1, wherein the sensing assembly is disposed in the second channel.

3. The subsurface safety valve of claim 2, further comprising compensation bellows disposed in the second channel between the first junction and the sensing assembly.

4. The subsurface safety valve of claim 3, further comprising a filter disposed between the second junction and the check valve.

5. The subsurface safety valve of claim 1, wherein the sensing assembly comprises a plurality of components operable to measure the degradation level of the fluid in the fluid circuit.

6. The subsurface safety valve of claim 5, wherein the plurality of components comprises an optical source and a photometer.

7. The subsurface safety valve of claim 6, wherein the plurality of components comprises a conductor and a magnet.

8. The subsurface safety valve of claim 6, wherein the plurality of components comprises an impedance sensor that includes an internal micro-channel and two single-layer coils.

9. The subsurface safety valve of claim 6, wherein the plurality of components comprises a microfluidic circuit and a sensor, wherein the microfluidic circuit includes microchannel and two capacitance plates.

10. The subsurface safety valve of claim 1, wherein the sensing assembly is configured to transmit a determined degradation level by transmitting at least one of a voltage output, a current output, a pressure output, a time stamp, or a temperature output measured by the sensing assembly.

11. A subsurface safety valve assembly for controlling fluid flow in a wellbore, the subsurface safety valve assembly comprising:
    a monitoring sub defining a hydraulic circuit extending between a hydraulic connection port of the monitoring sub and a piston bore defined by the monitoring sub, the hydraulic circuit comprises:
        a first channel that extends from the hydraulic connection port to the piston bore with a check valve installed in the first channel that prevents flow from the hydraulic connection port to the piston bore through the first channel; and a second channel that branches off the first channel at a first junction between the hydraulic port and the check valve and rejoins the first channel at second junction between the check valve and the piston bore;

wherein the monitoring sub comprising a sensing assembly incorporated in a hydraulic circuit that is operable to measure a degradation level of fluid in the hydraulic circuit;

a safety valve attached to the monitoring sub and configured to be disposed downhole of the monitoring sub and in hydraulic communication with the monitoring sub, the safety valve comprising:

a closure mechanism moveable between an open position allowing flow through subsurface safety valve and a closed position limiting flow through the subsurface safety valve; and a piston disposed in the piston bore of the monitoring sub and operable to move the closure mechanism between its open and closed positions, the piston hydraulically activated by pressure applied to the piston by pressure transmitted through hydraulic circuit of the monitoring sub.

12. The subsurface safety valve assembly of claim 11, wherein the sensing assembly is disposed in the second channel.

13. The subsurface safety valve assembly of claim 12, further comprising compensation bellows disposed in the second channel between the first junction and the sensing assembly.

14. The subsurface safety valve assembly of claim 11, wherein the sensing assembly comprises a plurality of components operable to measure the degradation level of the fluid in the fluid circuit.

15. The subsurface safety valve assembly of claim 11, wherein the closure mechanism comprises a flapper pivotable between an open position allowing flow through subsurface safety valve and a closed position limiting flow through the subsurface safety valve.

16. A subsurface safety valve assembly for controlling fluid flow in a wellbore, the subsurface safety valve assembly comprising:

a monitoring sub defining a hydraulic circuit extending through the monitoring sub, the monitoring sub comprising a sensing assembly with a plurality of components incorporated in a hydraulic circuit and operable to measure and to transmit a degradation level of fluid in the hydraulic circuit by transmitting at least one of a voltage output, a current output, a pressure output, a time stamp, or a temperature output measured by the sensing assembly;

a safety valve configured to be disposed downhole of the monitoring sub and in hydraulic communication with the monitoring sub, the safety valve comprising:

a closure mechanism moveable between an open position allowing flow through subsurface safety valve and a closed position limiting flow through the subsurface safety valve; and a piston in contact with the closure mechanism and operable to move the closure mechanism between its open and closed positions, the piston hydraulically activated by pressure applied to the piston by pressure transmitted through hydraulic circuit of the monitoring sub.

17. The subsurface safety valve assembly of claim 16, wherein the plurality of components comprises an optical source and a photometer.

18. The subsurface safety valve assembly of claim 16, wherein the monitoring sub is attached to the safety valve and the hydraulic circuit extends between a hydraulic connection port of the monitoring sub and a piston bore defined by the monitoring sub.

19. The subsurface safety valve assembly of claim 18, wherein the hydraulic circuit comprises: a first channel that extends from the hydraulic connection port to the piston bore with a check valve installed in the first channel that prevents flow from the hydraulic connection port to the piston bore through the first channel; and a second channel that branches off the first channel at a first junction between the hydraulic port and the check valve and rejoins the first channel at second junction between the check valve and the piston bore.

* * * * *